United States Patent
Kobayashi et al.

(10) Patent No.: US 11,710,853 B2
(45) Date of Patent: Jul. 25, 2023

(54) NONAQUEOUS ELECTROLYTE, NONAQUEOUS ELECTROLYTE ENERGY STORAGE DEVICE, AND METHOD FOR PRODUCING NONAQUEOUS ELECTROLYTE ENERGY STORAGE DEVICE

(71) Applicant: GS Yuasa International Ltd., Kyoto (JP)

(72) Inventors: Tetsuhiro Kobayashi, Kyoto (JP); Yudai Kawasoe, Kyoto (JP); Kenta Nagamine, Kyoto (JP)

(73) Assignee: GS Yuasa International Ltd., Kyoto (JP)

( * ) Notice: Subject to any disclaimer, the term of this patent is extended or adjusted under 35 U.S.C. 154(b) by 0 days.

(21) Appl. No.: 17/410,520

(22) Filed: Aug. 24, 2021

(65) Prior Publication Data

US 2021/0384555 A1  Dec. 9, 2021

Related U.S. Application Data

(62) Division of application No. 16/763,085, filed as application No. PCT/EP2018/081590 on Nov. 16, 2018, now abandoned.

(30) Foreign Application Priority Data

Nov. 29, 2017  (JP) .................. 2017-229587

(51) Int. Cl.
*H01M 10/0567* (2010.01)
*C07D 239/26* (2006.01)
(Continued)

(52) U.S. Cl.
CPC ...... *H01M 10/0567* (2013.01); *C07D 239/26* (2013.01); *C07D 239/38* (2013.01);
(Continued)

(58) Field of Classification Search
None
See application file for complete search history.

(56) References Cited

U.S. PATENT DOCUMENTS 6,245,458 B1 * 6/2001 Sotomura ............ H01M 4/364
429/231.95
6,630,272 B1  10/2003 Iwamoto et al.
(Continued)

FOREIGN PATENT DOCUMENTS

CN   103094615 A   5/2013
EP   1150373 A1   10/2001
(Continued)

OTHER PUBLICATIONS

S. Nowak et al., 162 Journal of The Electrochemical Society (2015) (Year: 2015).*

(Continued)

*Primary Examiner* — Alexander R Pagano
(74) *Attorney, Agent, or Firm* — Rankin, Hill & Clark LLP

(57) ABSTRACT

Provided are a nonaqueous electrolyte capable of providing a nonaqueous electrolyte energy storage device with reduced direct current resistance and an increased capacity retention ratio after charge-discharge cycles, a nonaqueous electrolyte energy storage device including such a nonaqueous electrolyte, and a method for producing such a nonaqueous electrolyte energy storage device. One mode of the present invention is a nonaqueous electrolyte for an energy storage device, containing an additive represented by the following Formula (1) or Formula (2). In Formula (1), $R^1$ to $R^4$ are each independently a hydrogen atom or a group represented by $-NR^a_2$, $-OR^a$, $-SR^a$, etc., with the proviso that at least one of $R^1$ to $R^4$ is a group represented by $-OR^a$, $-SR^a$, $-COOR^a$, $-COR^a$, $-SO_2R^a$, or $-SO_3R^a$. In Formula (2), $R^5$ to $R^7$ are each independently a hydrogen atom or a group represented by $-NR^b_2$, $-OR^b$, or $-SR^b$, with the proviso that at least one of $R^5$ to $R^7$ is a group represented by $-SR^b$.

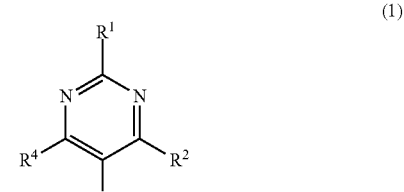

(1)

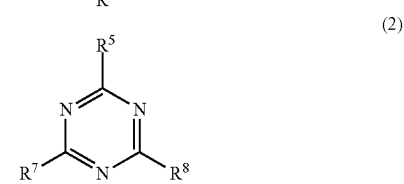

(2)

6 Claims, 1 Drawing Sheet

(51) Int. Cl.

| | | |
|---|---|---|
| *C07D 239/38* | (2006.01) | |
| *C07D 239/52* | (2006.01) | |
| *C07D 239/54* | (2006.01) | |
| *C07D 251/24* | (2006.01) | |
| *C07D 251/30* | (2006.01) | |
| *C07D 251/38* | (2006.01) | |
| *C07D 251/46* | (2006.01) | |
| *H01G 11/06* | (2013.01) | |
| *H01G 11/60* | (2013.01) | |
| *H01G 11/62* | (2013.01) | |
| *H01G 11/64* | (2013.01) | |
| *H01M 10/0525* | (2010.01) | |
| *H01M 10/0568* | (2010.01) | |
| *H01M 10/0569* | (2010.01) | |
| *H01G 11/50* | (2013.01) | |

(52) U.S. Cl.
CPC ......... *C07D 239/52* (2013.01); *C07D 239/54* (2013.01); *C07D 251/24* (2013.01); *C07D 251/30* (2013.01); *C07D 251/38* (2013.01); *C07D 251/46* (2013.01); *H01G 11/06* (2013.01); *H01G 11/60* (2013.01); *H01G 11/62* (2013.01); *H01G 11/64* (2013.01); *H01M 10/0525* (2013.01); *H01M 10/0568* (2013.01); *H01M 10/0569* (2013.01); *H01G 11/50* (2013.01); *H01M 2300/0025* (2013.01)

(56) References Cited

U.S. PATENT DOCUMENTS

| | | | | |
|---|---|---|---|---|
| 2003/0007038 | A1* | 1/2003 | Nakatani | B41J 2/1623 347/72 |
| 2003/0190530 | A1* | 10/2003 | Yang | H01M 50/571 429/339 |
| 2006/0269844 | A1 | 11/2006 | Deng et al. | |
| 2007/0148545 | A1 | 6/2007 | Amine et al. | |
| 2011/0129738 | A1 | 6/2011 | Kawashima | |
| 2012/0171579 | A1 | 7/2012 | Tsai et al. | |
| 2013/0004859 | A1 | 1/2013 | Yu et al. | |
| 2013/0230770 | A1 | 9/2013 | Oya et al. | |
| 2013/0244120 | A1* | 9/2013 | Yu | H01M 10/0567 429/339 |
| 2013/0252113 | A1 | 9/2013 | Yu et al. | |
| 2014/0057161 | A1 | 2/2014 | Kim et al. | |
| 2017/0346127 | A1* | 11/2017 | Zhang | H01M 4/62 |
| 2018/0013168 | A1* | 1/2018 | Yu | H01M 10/0569 |
| 2018/0301693 | A1* | 10/2018 | Choi | H01M 4/134 |
| 2020/0087473 | A1* | 3/2020 | Murdock | C08J 5/18 |
| 2020/0243906 | A1* | 7/2020 | Zhang | H01M 10/0569 |

FOREIGN PATENT DOCUMENTS

| | | | | |
|---|---|---|---|---|
| EP | 1150373 A1 * | 10/2001 | | H01G 11/58 |
| EP | 2063483 A1 | 5/2009 | | |
| EP | 2541663 A1 * | 1/2013 | | H01M 10/052 |
| EP | 2541663 A1 | 1/2013 | | |
| JP | 02162658 A * | 6/1990 | | H01M 10/08 |
| JP | 07057781 A * | 3/1995 | | |
| JP | 07057782 A * | 3/1995 | | |
| JP | 10-50344 A | 2/1998 | | |
| JP | 2001-273927 A | 10/2001 | | |
| JP | 2003-208920 A | 7/2003 | | |
| JP | 2003208920 A * | 7/2003 | | |
| JP | 2011-119097 A | 6/2011 | | |
| JP | 2013-16488 A | 1/2013 | | |
| JP | 2014071950 A * | 4/2014 | | |
| JP | 2015-122322 A | 7/2015 | | |
| JP | 2017152298 A * | 8/2017 | | |
| KR | 2004-0061562 A | 7/2004 | | |
| KR | 2004061562 A * | 7/2004 | | H01M 10/052 |
| KR | 2015-0019994 A | 2/2015 | | |
| WO | 2012-067102 A1 | 5/2012 | | |
| WO | 2013-012248 A2 | 1/2013 | | |
| WO | 2013-012250 A2 | 1/2013 | | |

OTHER PUBLICATIONS

A. Ahmed et al., 32 Journal of Dispersion Science and Technology, 453-463 (2011) (Year: 2011).*
T. Kobayashi et al., JP 2017229587 Notice of Reasons for Refusal (Translated), (Aug. 21, 2021) (Year: 2021).*
CAS Abstract and Indexed Compounds, M. Onuki et al., JP 2003208920 (2003) (Year: 2003).*
T. Kobayashi et al., JP 2017229587, Reconsideration Report by Examiner before Appeal (Translated) (Sep. 21, 2022) (Year: 2022).*
M. Liu et al., 138 J. Electrochem. Soc. (1991) (Year: 1991).*
International Search Report (ISR) dated Apr. 25, 2019 filed in PCT/EP2018/081590.

* cited by examiner

NONAQUEOUS ELECTROLYTE, NONAQUEOUS ELECTROLYTE ENERGY STORAGE DEVICE, AND METHOD FOR PRODUCING NONAQUEOUS ELECTROLYTE ENERGY STORAGE DEVICE

TECHNICAL FIELD

The present invention relates to a nonaqueous electrolyte, a nonaqueous electrolyte energy storage device, and a method for producing a nonaqueous electrolyte energy storage device.

BACKGROUND ART

Nonaqueous electrolyte secondary batteries, such as lithium ion secondary batteries, have been often used, for their high energy densities, in electronic devices such as personal computers and communication terminals, automobiles, and the like. Such a nonaqueous electrolyte secondary battery generally has a pair of electrodes electrically isolated by a separator and a nonaqueous electrolyte interposed between the electrodes, and is configured to be charged and discharged by transferring ions between the electrodes. In addition, as nonaqueous electrolyte energy storage devices other than nonaqueous electrolyte secondary batteries, capacitors, such as lithium ion capacitors and electric double layer capacitors, have also widely spread.

In nonaqueous electrolytes for nonaqueous electrolyte energy storage devices, various additives are added for the purpose of improving the performance etc. For example, in Patent Documents 1 and 2, a nonaqueous electrolyte solution for a lithium secondary battery containing a specific heterocyclic compound having a pyrimidine structure or a triazine structure has been proposed.

PRIOR ART DOCUMENTS

Patent Documents

Patent Document 1: JP-A-2015-122322
Patent Document 2: JP-A-2013-016488

SUMMARY OF THE INVENTION

Problems to be Solved by the Invention

The performance required for such a nonaqueous electrolyte energy storage device includes low direct current resistance, a high capacity retention ratio after charge-discharge cycles, and the like. However, even in an energy storage device using a nonaqueous electrolyte containing a heterocyclic compound such as pyrimidine or triazine, the initial direct current resistance and the capacity retention ratio after charge-discharge cycles are not necessarily sufficient.

The present invention has been made under the above circumstances, and an object thereof is to provide a nonaqueous electrolyte capable of providing a nonaqueous electrolyte energy storage device with reduced direct current resistance and an increased capacity retention ratio after charge-discharge cycles, a nonaqueous electrolyte energy storage device including such a nonaqueous electrolyte, and a method for producing such a nonaqueous electrolyte energy storage device.

Means for Solving the Problems

One mode of the present invention made in order to solve the above problems is a nonaqueous electrolyte for an energy storage device, containing an additive represented by the following Formula (1) or Formula (2):

[Chemical Formula 1]

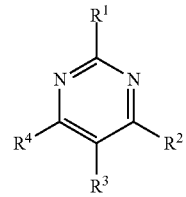

(1)

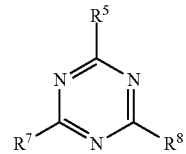

(2)

in Formula (1), $R^1$ to $R^4$ are each independently a hydrogen atom or a group represented by $—NR^a{}_2$, $—OR^a$, $—SR^a$, $—COOR^a$, $—COR^a$, $—SO_2R^a$, or $—SO_3R^a$, wherein $R^a$s are each independently a hydrogen atom or a hydrocarbon group, with the proviso that at least one of $R^1$ to $R^4$ is a group represented by $—OR^a$, $—SR^a$, $—COOR^a$, $—COR^a$, $—SO_2R^a$, or $—SO_3R^a$, and in Formula (2), $R^5$ to $R^7$ are each independently a hydrogen atom or a group represented by $—NR^b{}_2$, $—OR^b$, or $—SR^b$, wherein $R^b$s are each independently a hydrogen atom or a $C_{1-6}$ alkyl group, with the proviso that at least one of $R^5$ to $R^7$ is a group represented by $—SR^b$.

Another mode of the present invention made in order to solve the above problems is a nonaqueous electrolyte energy storage device having the above nonaqueous electrolyte.

Another mode of the present invention made in order to solve the above problems is a method for producing a nonaqueous electrolyte energy storage device using the above nonaqueous electrolyte.

Advantages of the Invention

According to the present invention, it is possible to provide a nonaqueous electrolyte capable of providing a nonaqueous electrolyte energy storage device with reduced direct current resistance and an increased capacity retention ratio after charge-discharge cycles, a nonaqueous electrolyte energy storage device including such a nonaqueous electrolyte, and a method for producing such a nonaqueous electrolyte energy storage device.

MODE FOR CARRYING OUT THE INVENTION

Figure 1:
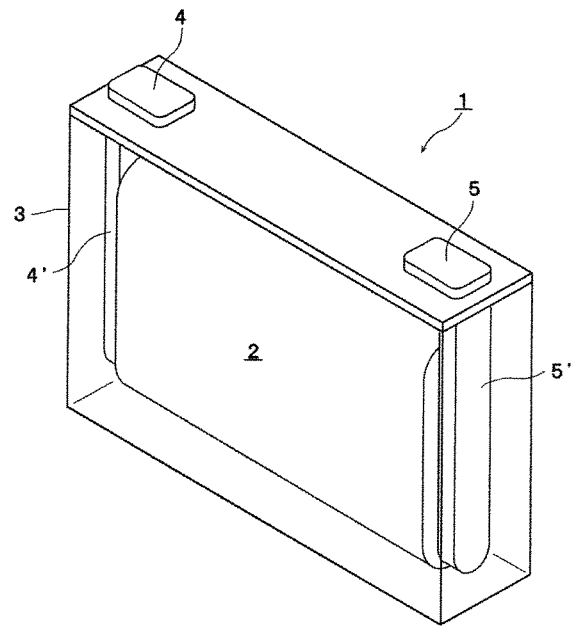
FIG. 1 is an appearance perspective view showing a nonaqueous electrolyte energy storage device according to one embodiment of the present invention.

A nonaqueous electrolyte according to one embodiment of the present invention is a nonaqueous electrolyte for an energy storage device, containing an additive represented by the following Formula (1) or Formula (2).

[Chemical Formula 2]

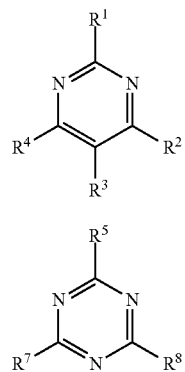

In Formula (1), $R^1$ to $R^4$ are each independently a hydrogen atom or a group represented by $-NR^a{}_2$, $-OR^a$, $-SR^a$, $-COOR^a$, $-COR^a$, $-SO_2R^a$, or $-SO_3R^a$, wherein $R^a$s are each independently a hydrogen atom or a hydrocarbon group, with the proviso that at least one of $R^1$ to $R^4$ is a group represented by $-OR^a$, $-SR^a$, $-COOR^a$, $-COR^a$, $-SO_2R^a$, or $-SO_3R^a$.

In Formula (2), $R^5$ to $R^7$ are each independently a hydrogen atom or a group represented by $-NR^b{}_2$, $-OR^b$, or $-SR^b$, wherein $R^b$s are each independently a hydrogen atom or a $C_{1-6}$ alkyl group, with the proviso that at least one of $R^5$ to $R^7$ is a group represented by $-SR^b$.

According to the nonaqueous electrolyte, the direct current resistance of a nonaqueous electrolyte energy storage device can be reduced, and also the capacity retention ratio after charge-discharge cycles can be increased. The reason for this is not clear, but is presumably as follows. In a conventional nonaqueous electrolyte containing a heterocyclic compound, it is believed that the heterocyclic compound forms a film on a negative electrode, thereby improving the charge-discharge cycle performance and the like. However, the formed film easily elutes into the nonaqueous solvent. Accordingly, it is believed that its effects are not sufficiently exerted. Meanwhile, in the above nonaqueous electrolyte, a heterocyclic compound having a specific substituent is used. It is believed that a film formed from such a heterocyclic compound has reduced solubility in a nonaqueous solvent. Therefore, presumably, according to the above nonaqueous electrolyte, an excellent film can be formed on a negative electrode, and, as a result, the direct current resistance of a nonaqueous electrolyte energy storage device can be reduced, and also the capacity retention ratio after charge-discharge cycles can be increased.

It is preferable that the additive is represented by Formula (1), and the $R^1$ to $R^4$ are each independently a hydrogen atom or a group represented by $-OR^a$, $-SR^a$, $-COOR^a$, $-COR^a$, $-SO_2R^a$, or $-SO_3R^a$. By using an additive having such a structure, the above effects of reducing the direct current resistance and increasing the capacity retention ratio can be further enhanced.

It is preferable that the additive is represented by Formula (1), and at least one of the $R^1$ to $R^4$ is a group represented by $-SR^a$, $-SO_2R^a$, or $-SO_3R^a$. By using an additive having such a structure, which has a sulfur-containing substituent, the above effects can be further enhanced.

It is preferable that the additive is represented by Formula (2), and the $R^5$ to $R^7$ are each independently a group represented by $-OR^b$ or $-SR^b$. By using an additive having such a structure, the above effects are enhanced. In addition, the initial capacity of a nonaqueous electrolyte energy storage device, as well as the coulomb efficiency and its retention ratio, are also increased. The reason for this is not clear, but is presumably that as a result of the introduction of a specific substituent, the film formation reaction is moderately suppressed, causing a decrease in the irreversible capacity.

A nonaqueous electrolyte energy storage device according to one embodiment of the present invention is a nonaqueous electrolyte energy storage device including the above nonaqueous electrolyte. The nonaqueous electrolyte energy storage device includes the above nonaqueous electrolyte and thus has low direct current resistance and also a high capacity retention ratio after charge-discharge cycles.

A method for producing a nonaqueous electrolyte energy storage device according to one embodiment of the present invention is a method for producing a nonaqueous electrolyte energy storage device using the above nonaqueous electrolyte. The method uses the above nonaqueous electrolyte and thus can produce a nonaqueous electrolyte energy storage device having low direct current resistance and also a high capacity retention ratio after charge-discharge cycles.

Hereinafter, a nonaqueous electrolyte, a nonaqueous electrolyte energy storage device, and a method for producing a nonaqueous electrolyte energy storage device according to one embodiment of the present invention will be described in detail.

<Nonaqueous Electrolyte>

The nonaqueous electrolyte contains a nonaqueous solvent, an electrolyte salt, and an additive. The nonaqueous electrolyte is for use in an energy storage device. Incidentally, the nonaqueous electrolyte is not limited to a liquid. That is, the nonaqueous electrolyte is not limited only to those in liquid state, and those in solid state, gel state, and the like are also encompassed.

(Nonaqueous Solvent)

As the nonaqueous solvent, known nonaqueous solvents commonly used as nonaqueous solvents for ordinary nonaqueous electrolytes for energy storage devices can be used. Examples of the nonaqueous solvents include cyclic carbonates, linear carbonates, esters, ethers, amides, sulfones, lactones, and nitriles. Among them, it is preferable to use at least a cyclic carbonate or a linear carbonate, and it is more preferable to use a cyclic carbonate and a linear carbonate together. In the case where a cyclic carbonate and a linear carbonate are used together, the volume ratio between the cyclic carbonate and the linear carbonate (cyclic carbonate: linear carbonate) is preferably, but not particularly limited to, 5:95 or more and 50:50 or less, for example.

Examples of the cyclic carbonates include ethylene carbonate (EC), propylene carbonate (PC), butylene carbonate (BC), vinylene carbonate (VC), vinyl ethylene carbonate (VEC), chloroethylene carbonate, fluoroethylene carbonate (FEC), difluoroethylene carbonate (DFEC), styrene carbonate, catechol carbonate, 1-phenylvinylene carbonate, and 1,2-diphenylvinylene carbonate. The cyclic carbonate preferably contains a fluorinated cyclic carbonate, and more preferably contains FEC.

Examples of the linear carbonates include diethyl carbonate (DEC), dimethyl carbonate (DMC), ethyl methyl carbonate (EMC), and diphenyl carbonate. The linear carbonate is preferably DMC or EMC.

(Electrolyte Salt)

As the electrolyte salt, known electrolyte salts commonly used as electrolyte salts for ordinary nonaqueous electrolytes for energy storage devices can be used. Examples of the electrolyte salts include lithium salts, sodium salts, potassium salts, magnesium salts, and onium salts, and lithium salts are preferable.

Examples of the lithium salts include inorganic lithium salts, such as $LiPF_6$, $LiPO_2F_2$, $LiBF_4$, $LiClO_4$, and $LiN(SO_2F)_2$, and lithium salts containing a fluorinated hydrocarbon group, such as $LiSO_3CF_3$, $LiN(SO_2CF_3)_2$, $LiN(SO_2C_2F_5)_2$, $LiN(SO_2CF_3)(SO_2C_4F_9)$, $LiC(SO_2CF_3)_3$, and $LiC(SO_2C_2F_5)_3$. Among them, inorganic lithium salts are preferable, and $LiPF_6$ is more preferable.

The lower limit of the content of the electrolyte salt in the nonaqueous electrolyte is preferably 0.1 mol/kg, more preferably 0.3 mol/kg, and still more preferably 0.5 mol/kg. Meanwhile, the upper limit is not particularly set, but is preferably 2.5 mol/kg, more preferably 2 mol/kg, and still more preferably 1.5 mol/kg.

(Additive)

The additive is a compound represented by the following Formula (1) or Formula (2). Because the nonaqueous electrolyte contains the above additive, the direct current resistance of a nonaqueous electrolyte energy storage device can be reduced, and also the capacity retention ratio after charge-discharge cycles can be increased. In addition, according to the nonaqueous electrolyte, the direct current resistance and the coulomb efficiency retention ratio after charge-discharge cycles of a nonaqueous electrolyte energy storage device can also be increased.

[Chemical Formula 3]

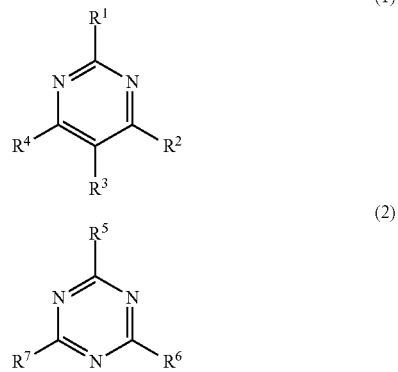

(Compound Represented by Formula (1))

In Formula (1), $R^1$ to $R^4$ are each independently a hydrogen atom or a group represented by $-NR^a{}_2$, $-OR^a$, $-SR^a$, $-COOR^a$, $-COR^a$, $-SO_2R^a$, or $-SO_3R^a$, wherein $R^a$s are each independently a hydrogen atom or a hydrocarbon group, with the proviso that at least one of $R^1$ to $R^4$ is a group represented by $-OR^a$, $-SR^a$, $-COOR^a$, $-COR^a$, $-SO_2R^a$, or $-SO_3R^a$.

Examples of hydrocarbon groups represented by $R^a$ include aliphatic hydrocarbon groups and aromatic hydrocarbon groups. Examples of aliphatic hydrocarbon groups include linear aliphatic hydrocarbon groups including alkyl groups such as a methyl group, an ethyl group, a propyl group, a butyl group, a pentyl group, and a hexyl group, alkenyl groups such as an ethenyl group and a propenyl group, alkynyl groups such as an ethynyl group and a propynyl group, and the like; and cycloaliphatic hydrocarbon groups including cycloalkyl groups such as a cyclohexyl group, cycloalkenyl groups such as a cyclohexenyl group, and the like. Examples of aromatic hydrocarbon groups include a phenyl group, a naphthyl group, a benzyl group, and a tolyl group. The hydrocarbon group is preferably an aliphatic hydrocarbon group, more preferably a linear aliphatic hydrocarbon group, still more preferably an alkyl group, still more preferably a $C_{1-6}$ alkyl group, and yet more preferably a methyl group.

$R^1$ is preferably a hydrogen atom, $-OR^a$, $-SR^a$, $-COOR^a$, $-COR^a$, $-SO_2R^a$, or $-SO_3R^a$, more preferably $-SR^a$, $-COOR^a$, $-SO_2R^a$, or $-SO_3R^a$, and still more preferably $-SR^a$, $-SO_2R^a$, or $-SO_3R^a$. In the case where $R^1$ is such a sulfur atom-containing group, the direct current resistance can be further reduced, and the capacity retention ratio can be further increased.

In addition, it is also preferable that $R^1$ is $-COOR^a$ or $-SO_2R^a$. At this time, it is preferable that $R^a$ is a hydrocarbon group. In the case where $R^1$ contains such an ester structure, so-called battery swelling accompanying charge-discharge cycles can be suppressed.

$R^2$ is preferably a hydrogen atom, $-OR^a$, $-SR^a$, $-COOR^a$, $-COR^a$, $-SO_2R^a$, or $-SO_3R^a$, and more preferably a hydrogen atom or $-OR^a$.

$R^3$ is preferably a hydrogen atom, $-OR^a$, $-SR^a$, $-COOR^a$, $-COR^a$, $-SO_2R^a$, or $-SO_3R^a$, and more preferably a hydrogen atom.

$R^4$ is preferably a hydrogen atom, $-OR^a$, $-SR^a$, $-COOR^a$, $-COR^a$, $-SO_2R^a$, or $-SO_3R^a$, and more preferably a hydrogen atom or $-OR^a$.

$R^a$ is preferably a hydrogen atom or an alkyl group, and more preferably a hydrogen atom or a methyl group.

In the case where $R^1$ to $R^4$ and $R^a$ are such groups, the above effects of the present invention can be further enhanced.

In addition, it is preferable that the above $R^1$ to $R^4$ are each independently a hydrogen atom or a group represented by $-OR^a$, $-SR^a$, $-COOR^a$, $-COR^a$, $-SO_2R^a$, or $-SO_3R^a$, more preferably a hydrogen atom or a group represented by $-OR^a$, $-SR^a$, $-COOR^a$, or $-SO_2R^a$. In the case where the compound represented by Formula (1) has such groups, the above effects are further enhanced.

It is preferable that at least one of the above $R^1$ to $R^4$ is a group represented by $-SR^a$, $-SO_2R^a$, or $-SO_3R^a$, more preferably a group represented by $-SR^a$ or $-SO_2R^a$. In the case where at least one of $R^1$ to $R^4$ is such a specific sulfur-containing substituent, the above effects can be further enhanced.

(Compound Represented by Formula (2))

In Formula (2), $R^5$ to $R^7$ are each independently a hydrogen atom or a group represented by $-NR^b{}_2$, $-OR^b$, or $-SR^b$, wherein $R^b$s are each independently a hydrogen atom or a $C_{1-6}$ alkyl group, with the proviso that at least one of $R^5$ to $R^7$ is a group represented by $-SR^b$.

Examples of $C_{1-6}$ alkyl groups represented by $R^b$ include a methyl group, an ethyl group, a propyl group, a butyl group, a pentyl group, and a hexyl group.

$R^5$ is preferably $-NR^b{}_2$ or $-SR^b$, and more preferably $-SR^b$.

$R^6$ and $R^7$ are each preferably $-SR^b$.

With respect to $R^b$, $R^b$ in $-NR^b{}_2$ is preferably a $C_{1-6}$ alkyl group, more preferably a $C_{3-5}$ alkyl group, and still more preferably a butyl group. In addition, $R^b$ in $-SR^b$ is preferably a hydrogen atom.

In the case where $R^5$ to $R^7$ and $R^b$ are such groups, the effects of the present invention can be further enhanced.

In addition, it is preferable that the above $R^5$ to $R^7$ are each independently a group represented by —$OR^b$ or —$SR^b$, more preferably a group represented by —$SR^b$. In the case where the compound represented by Formula (2) has such a group, the above effects are enhanced. In addition, the initial capacity of a nonaqueous electrolyte energy storage device, as well as the coulomb efficiency and its retention ratio, are also increased.

The lower limit of the content of the additive in the nonaqueous electrolyte is preferably 0.01 mass %, more preferably 0.05 mass %, still more preferably 0.1 mass %, yet more preferably 0.3 mass %, and sometimes yet more preferably 1 mass %. Meanwhile, the upper limit of the content is, for example, preferably 5 mass %, preferably 3 mass %, more preferably 2 mass %, sometimes still more preferably 1 mass %, and sometimes yet more preferably 0.5 mass %. When the content of the additive is not less than the above lower limit and not more than the above upper limit, the direct current resistance of a nonaqueous electrolyte energy storage device can be further reduced, and also the capacity retention ratio after charge-discharge cycles can be further increased, for example.

Incidentally, the additive is usually added as a molecule having a structure represented by Formula (1) or Formula (2). Therefore, it is believed that in the nonaqueous electrolyte, the additive is usually not present in the form of a salt but present as a molecule represented by Formula (1) or Formula (2). However, for coexistence with an electrolyte salt, part of the additive may be present in the form of a salt having the anion of the electrolyte salt as a counter-anion, for example.

(Other Components)

The nonaqueous electrolyte may further contain other components besides the nonaqueous solvent, the electrolyte salt, and the additive. Examples of the other components include 1,3-propenesultone (PRS), vinyl ethylene carbonate (VEC), vinylene carbonate (VC), adiponitrile (AN), diglycol sulfate (DGLST), pentyl glycol sulfate (PEGLST), propylene sulfate (PGLST), lithium bis(trifluoromethylsulfonyl) amide (LiTFSA), and lithium tetrafluoro(oxalate)phosphate (LiFOP). Among them, PRS, VC, and AN are preferable. These components are capable of forming an excellent film on a negative electrode to further enhance the effects of the present invention. In addition, when these components are used together with the additive, the initial discharge capacity and direct current resistance, the direct current resistance retention ratio after charge-discharge cycles, and the like can be improved. Incidentally, the lower limit of the content of other components in the nonaqueous electrolyte is preferably 0.01 mass %, more preferably 0.1 mass %, and still more preferably 0.5 mass %. Meanwhile, the upper limit of the content is preferably 5 mass %, and more preferably 2 mass %.

The nonaqueous electrolyte can usually be obtained by adding an electrolyte salt, the above additive, and optionally other components to the nonaqueous solvent and dissolving them.

<Nonaqueous Electrolyte Energy Storage Device>

A nonaqueous electrolyte energy storage device according to one embodiment of the present invention includes a positive electrode, a negative electrode, and a nonaqueous electrolyte. Hereinafter, as an example of the nonaqueous electrolyte energy storage device, a nonaqueous electrolyte secondary battery (hereinafter sometimes simply referred to as "secondary battery") will be described. The positive electrode and negative electrode are usually alternately stacked by laminating or winding via a separator to form an electrode assembly. The electrode assembly is stored in a case, and the case is filled with a nonaqueous electrolyte. As the nonaqueous electrolyte, the nonaqueous electrolyte according to one embodiment of the present invention described above is used. The nonaqueous electrolyte is interposed between the positive electrode and the negative electrode. As the case, a known metal case, resin case, or the like commonly used as a case of a secondary battery can be used. Hereinafter, the constituent elements of the secondary battery other than the nonaqueous electrolyte will be described.

(Positive Electrode)

The positive electrode includes a positive electrode substrate and a positive active material layer placed on the positive electrode substrate directly or via an intermediate layer.

The positive electrode substrate is electrically conductive. As materials for the substrate, metals such as aluminum, titanium, tantalum, and stainless steel or alloys thereof are used. Among them, in terms of the balance of potential resistance, high electrical conductivity, and cost, aluminum and an aluminum alloy are preferable. In addition, the positive electrode substrate may be in the form of a foil, a deposited film, or the like, and, in terms of cost, a foil is preferable. That is, as the positive electrode substrate, an aluminum foil is preferable. Incidentally, examples of aluminum and an aluminum alloy include A1085P and A3003P specified in JIS-H-4000 (2014).

The intermediate layer is a coating layer on the surface of the positive electrode substrate and contains electrically conductive particles such as carbon particles, thereby reducing the contact resistance between the positive electrode substrate and the positive active material layer. The intermediate layer is not particularly limited in configuration, and can be formed, for example, from a composition containing a resin binder and electrically conductive particles. Incidentally, "electrically conductive" means that the volume resistivity measured in accordance with JIS-H-0505 (1975) is $10^7$ Ω·cm or less, while "electrically non-conductive" means that the volume resistivity is more than $10^7$ Ω·cm.

The positive active material layer is formed from a so-called positive electrode mixture containing a positive active material. In addition, the positive electrode mixture forming the positive active material layer contains optional components, such as conductive agents, binders (binding agents), thickening agents, and fillers, as necessary.

Examples of the positive active materials include composite oxides represented by $Li_xMO_y$ (M represents at least one kind of transition metal) (oxides having a layered α-$NaFeO_2$ crystal structure, such as $Li_xCoO_2$, $Li_xNiO_2$, $Li_xMnO_3$, $Li_xNi_\alpha Co_{(1-\alpha)}O_2$, $Li_xNi_\alpha Co_\beta Al_{(1-\alpha-\beta)}O_2$, $Li_xNi_\alpha Mn_\beta Co_{(1-\alpha-\beta)}O_2$, and $Li_{1+x}(Ni_\alpha Mn_\beta Co_{(1-\alpha-\beta)})_{1-x}O_2$, and oxides having a spinel crystal structure, such as $Li_xMn_2O_4$ and $Li_xNi_\alpha Mn_{(2-\alpha)}O_4$) and polyanion compounds represented by $Li_wMe_x(XO_y)_z$ (Me represents at least one kind of transition metal, and X represents P, Si, B, V, or the like, for example) ($LiFePO_4$, $LiMnPO_4$, $LiNiPO_4$, $LiCoPO_4$, $Li_3V_2(PO_4)_3$, $Li_2MnSiO_4$, $Li_2CoPO_4F$, etc.). The elements or polyanions in these compounds may be partially substituted with other elements or anion species. In the positive active material layer, these compounds may be used alone, and it is also possible to use a mixture of two or more kinds.

The conductive agents are not particularly limited. Examples of such conductive agents include natural or artificial graphite, carbon black such as furnace black, acetylene black, and ketjen black, metals, and electrically conductive ceramics, and acetylene black is preferable. The conductive agent may be in the form of a powder, fibers, or the like.

Examples of the binders (binding agents) include thermoplastic resins such as fluororesins (polytetrafluoroethylene (PTFE), polyvinylidene fluoride (PVDF), etc.), polyethylene, polypropylene, and polyimide; elastomer such as ethylene-propylene-diene rubber (EPDM), sulfonated EPDM, styrene-butadiene rubber (SBR), and fluororubber; and polysaccharide polymers.

Examples of the thickening agents include polysaccharide polymers such as carboxymethylcellulose (CMC) and methyl cellulose. In addition, in the case where the thickening agent has a functional group that reacts with lithium, it is preferable that the functional group is previously deactivated by methylation or the like.

The fillers are not particularly limited. The filler may contain, as a main component, a polyolefin such as polypropylene or polyethylene, silica, alumina, zeolite, glass, or the like.

(Negative Electrode)

The negative electrode includes a negative electrode substrate and a negative active material layer placed on the negative electrode substrate directly or via an intermediate layer. The intermediate layer may have the same configuration as that of the intermediate layer of the positive electrode.

The negative electrode substrate may have the same configuration as that of the positive electrode substrate. However, as materials therefor, metals such as copper, nickel, stainless steel, and nickel-plated steel or alloys thereof are used, and copper or a copper alloy is preferable. That is, as the negative electrode substrate, a copper foil is preferable. Examples of copper foils include rolled copper foils and electrolytic copper foils.

The negative active material layer is formed from a so-called negative electrode mixture containing a negative active material. In addition, the negative electrode mixture forming the negative active material layer contains optional components, such as conductive agents, binders, thickening agents, and fillers, as necessary. As the optional components such as conductive agents, binding agents, thickening agents, and fillers, the same components as those for the positive active material layer can be used.

As the negative active material, usually, a material capable of occluding and releasing lithium ions is used. Specific examples of negative active materials include metals or semimetals, such as Si and Sn; metal oxides or semimetal oxides, such as Si oxide and Sn oxide; polyphosphoric acid compounds; and carbon materials such as black lead (graphite) and non-graphite carbon (graphitizable carbon or non-graphitizable carbon).

Further, the negative electrode mixture (negative active material layer) may also contain typical non-metal elements such as B, N, P, F, Cl, Br, and I, typical metal elements such as Li, Na, Mg, Al, K, Ca, Zn, Ga, and Ge, and transition metal elements such as Sc, Ti, V, Cr, Mn, Fe, Co, Ni, Cu, Mo, Zr, Ta, Hf, Nb, and W.

(Separator)

As a material of the separator, for example, a woven fabric, a nonwoven fabric, a porous resin film, or the like is used. Among them, a porous resin film is preferable in terms of strength, and a nonwoven fabric is preferable in terms of nonaqueous electrolyte-holding properties. As a main component of the separator, a polyolefin such as polyethylene or polypropylene is preferable in terms of strength, for example, and polyimide, aramid, or the like is preferable in terms of resistance to oxidative degradation, for example. In addition, a composite resin thereof may also be used.

Incidentally, an inorganic layer may be disposed between the separator and an electrode (usually the positive electrode). This inorganic layer is a porous layer, which is also called a heat-resistant layer or the like. In addition, it is also possible to use a separator in which an inorganic layer is formed on one side of a porous resin film. The inorganic layer is usually formed of inorganic particles and a binder, and may also contain other components.

<Method for Producing Nonaqueous Electrolyte Energy Storage Device>

A method for producing a nonaqueous electrolyte energy storage device according to one embodiment of the present invention is a method for producing a nonaqueous electrolyte energy storage device using the above nonaqueous electrolyte. The method is not particularly limited except for using the nonaqueous electrolyte containing the additive represented by Formula (1) or Formula (2) described above. In the case of the secondary battery described above, for example, the method includes a step of producing a positive electrode, a step of producing a negative electrode, a step of preparing a nonaqueous electrolyte, a step of alternatively stacking the positive electrode and the negative electrode by laminating or winding via a separator to form an electrode assembly, a step of housing the positive electrode and the negative electrode (electrode assembly) in a case, and a step of injecting the nonaqueous electrolyte into the case. After the injection, the injection port is sealed to complete the production.

<Other Embodiments>

The present invention is not limited to the above embodiment, and can be implemented, in addition to the above modes, in various modified or improved modes. For example, it is also possible that the positive electrode and the negative electrode are not provided with an intermediate layer and do not have a clear layer structure. For example, the positive electrode and the negative electrode may have a structure in which the active material is loaded on a mesh substrate. In addition, although a mode in which the nonaqueous electrolyte energy storage device is a secondary battery has mainly been described in the above embodiment, other nonaqueous electrolyte energy storage devices are also possible. Examples of other nonaqueous electrolyte energy storage devices include capacitors (electric double layer capacitors, lithium ion capacitors).

FIG. 1 shows a schematic diagram of a rectangular nonaqueous electrolyte energy storage device 1 (nonaqueous electrolyte secondary battery), which is one embodiment of the nonaqueous electrolyte energy storage device according to the present invention. Incidentally, the figure is a perspective view showing the inside of the case. In the nonaqueous electrolyte energy storage device 1 shown in FIG. 1, an electrode assembly 2 and a nonaqueous electrolyte are stored in a case 3. The electrode assembly 2 is formed by winging a positive electrode provided with a positive active material and a negative electrode provided with a negative active material via a separator. The positive electrode is electrically connected to the positive electrode terminal 4 via a positive electrode lead 4', while the negative electrode is electrically connected to the negative electrode terminal 5 via a negative electrode lead 5'.

Figure 2:
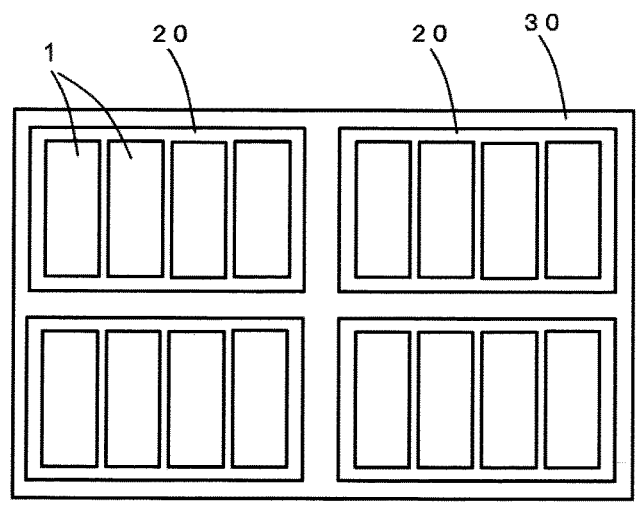
FIG. 2 is a schematic diagram showing an energy storage apparatus formed by assembling a plurality of nonaqueous electrolyte energy storage devices according to one embodiment of the present invention.

The configuration of the nonaqueous electrolyte energy storage device according to the present invention is not particularly limited, and examples thereof include a cylindrical battery, a prismatic battery (rectangular battery), and a flat battery. The present invention can also be implemented as an energy storage apparatus provided with a plurality of the above nonaqueous electrolyte energy storage devices. FIG. 2 shows one embodiment of the energy storage apparatus. In FIG. 2, an energy storage apparatus 30 includes a plurality of energy storage units 20. Each energy storage unit 20 includes a plurality of nonaqueous electrolyte energy storage devices 1. The energy storage device 30 can be mounted as an automotive power supply on electric vehicles (EV), hybrid vehicles (HEV), plug-in hybrid vehicles (PHEV), and the like, and can also be used as a stationary power supply for backup.

EXAMPLES

Hereinafter, the present invention will be described in further detail with reference to examples. However, the present invention is not limited to the following examples.

The additives used in the examples and comparative examples are as follows.

MPC: Compound represented by the following Formula (1a)

DMSP: Compound represented by the following Formula (1b)

MCP: Compound represented by the following Formula (1c)

PMD: Compound represented by the following Formula (1x)

[Chemical Formula 4]

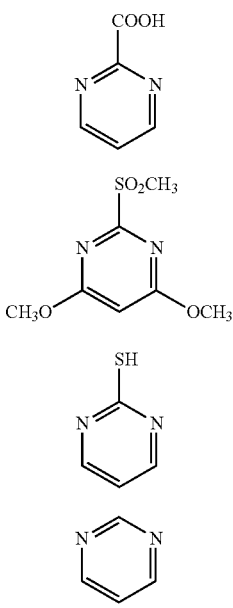

TCA: Compound represented by the following Formula (2a)

DTD: Compound represented by the following Formula (2b)

TAZ: Compound represented by the following Formula (2x)

TAC: Compound represented by the following Formula (2y)

[Chemical Formula 5]

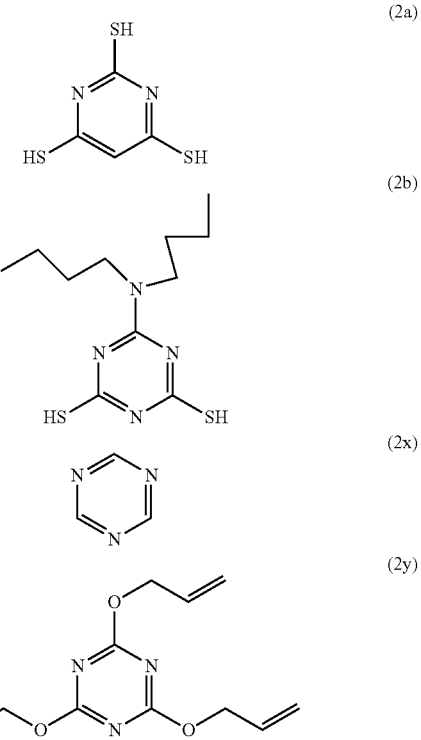

PRS: 1,3-Propenesultone
VC: Vinylene carbonate
AN: Adiponitrile

Example 1

(Preparation of Nonaqueous Electrolyte)

In a nonaqueous solvent obtained by mixing FEC, DMC and EMC in a volume ratio of 10:40:50, $LiPF_6$ was dissolved as an electrolyte salt at a concentration of 1.2 mol/L, and 2.0 mass % MPC was added thereto as an additive, thereby obtaining a nonaqueous electrolyte of Example 1.

(Production of Nonaqueous Electrolyte Energy Storage Device)

Using the above nonaqueous electrolyte, a nonaqueous electrolyte energy storage device (secondary battery) of Example 1 was obtained as follows.

(Production of Positive Electrode)

As a positive active material, a positive electrode paste containing $LiNi_{0.8}Co_{0.15}Al_{0.05}O_2$, acetylene black, and polyvinylidene fluoride in a mass ratio of 91:4.5:4.5 and having N-methyl-2-pyrrolidone as a solvent (dispersion medium) was prepared. The positive electrode paste was applied to the surface of an aluminum foil, followed by pressure molding using a roller press to form a positive active material layer. Subsequently, drying at reduced pressure was performed at 100° C. for 12 hours, thereby obtaining a positive electrode.

(Production of Negative Electrode)

As a negative active material, a negative electrode paste containing graphite, a styrene-butadiene rubber, and carboxymethylcellulose in a mass ratio of 95:2:3 and having water as a solvent (dispersion medium) was prepared. The negative electrode paste was applied to the surface of a copper foil, followed by pressure molding using a roller press to form a negative active material layer. Subsequently, drying at reduced pressure was performed at 100° C. for 12 hours, thereby obtaining a negative electrode.
(Assembly)

The positive electrode and the negative electrode were wound via a porous resin film separator made of polyolefin to form an electrode assembly. The electrode assembly was inserted into an aluminum case, and then the case lid was laser-welded. The nonaqueous electrolyte described above was injected into the case through an electrolyte solution filling hole provided in the case, and then the electrolyte solution filling hole was sealed, thereby obtaining a nonaqueous electrolyte secondary battery.

Examples 2 to 7 and Comparative Examples 1 to 5

Nonaqueous electrolytes and nonaqueous electrolyte energy storage devices of Examples 2 to 7 and Comparative Examples 1 to 5 were obtained in the same manner as in Example 1, except that the kinds and amounts of additives shown in Tables 1 to 3 were added as additives.

[Evaluation]
(Initial Performance Evaluation)

As a capacity confirmation test, each nonaqueous electrolyte energy storage device was subjected to 0.33 C constant current charge at 25° C. to 4.35 V, followed by 4.35 V constant voltage charge. The charge was completed when the total charge time reached 5 hours. After the charge, a rest period of 10 minutes was given, and then 1.0 C constant current discharge was performed at 25° C. to 2.50 V. In this manner, the initial discharge capacity was determined. In addition, the direct current resistance (DCR) at 50% SOC, 25° C. or −10° C., was measured. In the examples and comparative example of Table 1, the thickness of each nonaqueous electrolyte energy storage device was measured. In Example 4 and Comparative Example 2 of Table 2, the discharge capacity in the capacity confirmation test was divided by the amount of charge to determine the coulomb efficiency (%). Some of the measurement results are shown in Tables 1 to 3.

Incidentally, the measurement results are expressed as relative values based on the value of the comparative example to be compared. That is, Examples 1 to 3 of Table 1 show relative values based on Comparative Example 1, Examples 4 and 5 and Comparative Example 3 of Table 2 show relative values based on Comparative Example 2, and Example 6 of Table 3 shows relative values based on Comparative Example 4, while Example 7 shows relative values based on Comparative Example 5. The same applies to the results of the performance evaluation after charge-discharge cycles described below.

(Charge-Discharge Cycle Test)

Each nonaqueous electrolyte energy storage device was subjected to the following cycle test. At 45° C., constant current constant voltage charge was performed at a charge current of 0.33 C to an end-of-charge voltage of 4.35 V. The charge was completed when the total charge time reached 5 hours. Subsequently, a rest period of 10 minutes was given. Subsequently, constant current discharge was performed at a discharge current of 1.0 C to an end-of-discharge voltage of 2.50 V, followed by a rest period of 10 minutes. In all the examples and comparative examples, five hundred cycles of this charge-discharge were performed.

(Performance Evaluation after Charge-Discharge Cycles)

In the examples and comparative examples of Tables 1 and 2, after the cycle test, a capacity confirmation test was performed in the same manner as in the above "Initial Performance Evaluation." The capacity after the charge-discharge cycle test was divided by the initial capacity to determine the capacity retention ratio after charge-discharge cycles (capacity retention ratio).

In the examples and comparative example of Table 1, after the cycle test, the thickness of each nonaqueous electrolyte energy storage device was measured, and the thickness after the charge-discharge cycle test was divided by the initial thickness to determine the thickness retention ratio after charge-discharge cycles.

In the examples and comparative example of Table 1, after the cycle test, the direct current resistance (DCR) at 50% SOC, 25° C., was measured in the same manner as in the above "Initial Performance Evaluation." The DCR after the charge-discharge cycle test was divided by the initial DCR to determine the DCR retention ratio after charge-discharge cycles.

In Example 4 and Comparative Example 2 of Table 2, in a capacity confirmation test after the cycle test, the amount of charge and the discharge capacity were measured, the discharge capacity was divided by the amount of charge to determine the coulomb efficiency (%). The coulomb efficiency after the charge-discharge cycle test was divided by the initial coulomb efficiency to determine the coulomb efficiency retention ratio after charge-discharge cycles.

In the examples and comparative examples of Table 3, after the cycle test, in the same manner as in the above "Initial Performance Evaluation", a capacity confirmation test was performed, and the direct current resistance (DCR) at 50% SOC, 25° C. or −10° C., was measured.

The measurement results are shown in Tables 1 to 3 as relative values each based on the value of the comparative example to be compared. Incidentally, "-" in the tables means that the measurement was not performed.

TABLE 1

| | Additive | | Initial DCR | Retention ratio after charge-discharge cycles (after cycles/before cycles) | | |
|---|---|---|---|---|---|---|
| | Kind | Content (mass %) | (25° C.)(*1) (%) | Capacity (*1) (%) | Thickness (*1) (%) | DCR (25° C.)(*1) (%) |
| Example 1 | MPC | 2.0 | 66 | 138 | 96 | 98 |
| Example 2 | DMSP | 0.5 | 50 | 160 | 98 | 91 |
| Example 3 | MCP | 0.3 | 49 | 162 | 101 | 87 |
| Comparative Example 1 | PMD | 2.0 | 100 | 100 | 100 | 100 |

(*1)Relative values based on Comparative Example 1 (as 100%)

TABLE 2

| | Additive | | Initial | | | Retention ratio after charge-discharge cycles (after cycles/before cycles) | |
|---|---|---|---|---|---|---|---|
| | Kind | Content (mass %) | Capacity (*2) (%) | DCR (25° C.)(*2) (%) | Coulomb efficiency (*2) (%) | Capacity (*2) (%) | Coulomb efficiency (*2) (%) |
| Example 4 | TCA | 0.4 | 103 | 54 | 101 | 107 | 107 |
| Example 5 | DTD | 0.5 | 101 | 54 | — | 107 | — |
| Comparative Example 2 | TAZ | 2.0 | 100 | 100 | 100 | 100 | 100 |
| Comparative Example 3 | TAC | 2.0 | 102 | 133 | — | — | — |

(*2) Relative values based on Comparative Example 2 (as 100%).

TABLE 3

| | Additive | | Initial | | After charge-discharge cycles | | |
|---|---|---|---|---|---|---|---|
| | Kind | Content (mass %) | Capacity (*3) (%) | DCR (25° C.)(*3) (%) | Capacity (*3) (%) | DCR (25° C.)(*3) (%) | DCR (−10° C.)(*3) (%) |
| Example 6 | PRS | 2.0 | 100.3 | 99.3 | 100.3 | 99.8 | 99.4 |
| | TCA | 0.05 | | | | | |
| Comparative Example 4 | PRS | 2.0 | 100.0 | 100.0 | 100.0 | 100.0 | 100.0 |
| Example 7 | VC | 1.0 | 100.4 | 99.9 | 100.9 | 96.1 | 97.3 |
| | AN | 0.5 | | | | | |
| | TCA | 0.05 | | | | | |
| Comparative Example 5 | VC | 1.0 | 100.0 | 100.0 | 100.0 | 100.0 | 100.0 |
| | AN | 0.5 | | | | | |

(*3) Example 6 shows relative values based on Comparative Example 4 (as 100%). Example 7 shows relative values based on Comparative Example 5 (as 100%).

As shown in the above Table 1 and Table 2, it can be seen that in Examples 1 to 5 using a nonaqueous electrolyte containing an additive represented by Formula (1) or Formula (2) (MPC, DMSP, MCP, TCA, and DTD), the initial DCR is low, and also the capacity retention ratio after charge-discharge cycles is high.

Further, as shown in Table 1, it can be seen that in Examples 1 to 3 using an additive represented by Formula (1), an increase in DCR after charge-discharge cycles is also suppressed. Further, in Examples 2 and 3 using an additive wherein at least one of $R^1$ to $R^4$ in Formula (1) is a group represented by $-SR^a$, $-SO_2R^a$, or $-SO_3R^a$, the initial DCR is particularly low, and also the capacity retention ratio and the DCR retention ratio after charge-discharge cycles are particularly excellent. In addition, it can be seen that in Examples 1 to 2, an increase in the thickness after charge-discharge cycles, so-called battery swelling, is also suppressed.

In addition, as shown in Table 2, it can be seen that in Example 4 using an additive represented by Formula (2), wherein $R^5$ to $R^7$ are each independently a group represented by $-OR^b$ or $-SR^b$, the initial discharge capacity and coulomb efficiency are increased, and also the coulomb efficiency retention ratio after charge-discharge cycles is high.

In addition, as shown in Table 3, it can be seen that when an additive represented by Formula (1) or Formula (2) is used together with other additives, there is a tendency that the initial discharge capacity and DCR are improved, and the capacity and DCR after charge-discharge cycles are also improved. In particular, it can be seen that an increase in DCR at a low temperature (−10° C.) is suppressed.

INDUSTRIAL APPLICABILITY

The present invention is applicable to a nonaqueous electrolyte energy storage device used as a power supply for electronic devices such as personal computers and communication terminals, automobiles, and the like.

DESCRIPTION OF REFERENCE SIGNS

1: Nonaqueous electrolyte energy storage device
2: Electrode assembly
3: Case
4: Positive electrode terminal
4': Positive electrode lead
5: Negative electrode terminal
5': Negative electrode lead
20: Energy storage unit
30: Energy storage apparatus

The invention claimed is:

1. A nonaqueous electrolyte for an energy storage device, comprising a nonaqueous solvent, an electrolyte salt and an additive represented by the following Formula (1), wherein the electrolyte salt includes a lithium salt:

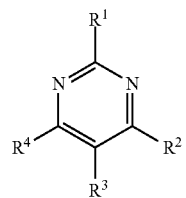

(1)

in Formula (1), $R^1$ to $R^4$ are each independently a hydrogen atom or a group represented by $-NR^a_2$, $-OR^a$, $-SR^a$, $-COOR^a$, $-COR^a$, $-SO_2R^a$, or $-SO_3R^a$, wherein $R^a$s are each independently a hydrogen atom or a hydrocarbon group, with the proviso that $R^1$ is a group represented by $-SR^a$, $-COOR^a$, $-COR^a$, $-SO_2R^a$, or $-SO_3R^a$.

2. The nonaqueous electrolyte according to claim 1, wherein
the $R^2$ to $R^4$ are each independently a hydrogen atom or a group represented by $-OR^a$, $-SR^a$, $-COOR^a$, $-COR^a$, $-SO_2R^a$, or $-SO_3R^a$.

3. A nonaqueous electrolyte energy storage device, comprising:
a positive electrode;
a negative electrode; and
the nonaqueous electrolyte according to claim 1.

4. A method for producing a nonaqueous electrolyte energy storage device comprising a positive electrode, a negative electrode and the nonaqueous electrolyte according to claim 1, the method comprising:
providing the nonaqueous electrolyte in a case of the nonaqueous electrolyte energy storage device.

5. The nonaqueous electrolyte energy storage device according to claim 3, wherein the nonaqueous electrolyte energy storage device is a lithium ion secondary battery or a lithium ion capacitor.

6. The method according to claim 4, wherein the nonaqueous electrolyte energy storage device is a lithium ion secondary battery or a lithium ion capacitor.

* * * * *